(12) United States Patent
Binninger et al.

(10) Patent No.: US 10,729,366 B2
(45) Date of Patent: Aug. 4, 2020

(54) SPHERICAL BIOMEDICAL SAMPLING AND MIXING CONTAINER

(71) Applicant: Fenwal, Inc., Lake Zurich, IL (US)

(72) Inventors: Steven C. Binninger, Evanston, IL (US); Divya Patil Hangargekar, Wheeling, IL (US)

(73) Assignee: Fenwal, Inc., Lake Zurich, IL (US)

(*) Notice: Subject to any disclaimer, the term of this patent is extended or adjusted under 35 U.S.C. 154(b) by 0 days.

(21) Appl. No.: 14/558,144

(22) Filed: Dec. 2, 2014

(65) Prior Publication Data
US 2016/0151239 A1 Jun. 2, 2016

(51) Int. Cl.
A61B 5/15 (2006.01)
A61B 5/153 (2006.01)
B65D 83/38 (2006.01)

(52) U.S. Cl.
CPC ........ *A61B 5/150366* (2013.01); *A61B 5/153* (2013.01); *A61B 5/15003* (2013.01); *A61B 5/15032* (2013.01); *A61B 5/150221* (2013.01); *B65D 83/38* (2013.01)

(58) Field of Classification Search
CPC ............................... A61J 1/12; A61B 5/150366
See application file for complete search history.

(56) References Cited

U.S. PATENT DOCUMENTS

| | | | | |
|---|---|---|---|---|
| 3,529,599 A * | 9/1970 | Folkman | ................. | A61F 5/441 604/323 |
| 3,749,016 A * | 7/1973 | Hershkowitz | ........... | F42B 12/34 102/517 |
| 3,827,607 A * | 8/1974 | Schultz | ................... | B65D 83/64 222/389 |
| 3,877,614 A * | 4/1975 | Murphy | ................... | B05B 11/00 222/209 |
| 4,875,600 A * | 10/1989 | D'Hoogue | .............. | G01F 11/26 222/52 |
| 4,921,131 A * | 5/1990 | Binderbauer | .............. | A47K 5/12 220/4.25 |
| 5,330,464 A * | 7/1994 | Mathias | .............. | A61M 39/221 604/403 |
| 5,372,143 A * | 12/1994 | Bernes | ................. | A61M 39/02 600/575 |
| 5,454,208 A * | 10/1995 | Kawano | .................... | A61J 1/10 53/133.2 |
| 5,830,185 A * | 11/1998 | Block, Jr. | ........... | A61M 1/3627 604/122 |
| 6,287,289 B1 * | 9/2001 | Niedospial, Jr. | .......... | A61J 1/10 206/828 |
| 7,699,828 B2 | 4/2010 | Mathias et al. | | |

(Continued)

OTHER PUBLICATIONS

"Side Arm Flask at Thomas Scientific." Thomas Scientific. Oct. 6, 2014. Web. May 11, 2016. <http://www.thomassci.com/scientific-supplies/Side%20Arm%20Flask>.*

(Continued)

*Primary Examiner* — Sean P Dougherty
(74) *Attorney, Agent, or Firm* — Cook Alex Ltd.

(57) ABSTRACT

Biomedical containers for sampling and mixing biological fluids are disclosed. The biomedical containers are at least substantially spherical and include access sites for accessing the container interior. The containers may be included as part of a disposable biological fluid processing kit.

23 Claims, 4 Drawing Sheets

(56) References Cited

U.S. PATENT DOCUMENTS

| | | | |
|---|---|---|---|
| 8,632,624 B2* | 1/2014 | Cassidy | A61M 5/36 604/122 |
| 9,533,109 B2* | 1/2017 | Bryan | A61M 5/36 |
| 9,839,582 B2 | 12/2017 | Binninger | |
| 2002/0019621 A1* | 2/2002 | Mathias | A61B 5/1427 604/409 |
| 2004/0082899 A1* | 4/2004 | Mathias | A61M 1/0236 604/6.16 |
| 2005/0148993 A1* | 7/2005 | Mathias | A61B 5/15 604/409 |
| 2008/0112847 A1* | 5/2008 | Chen | G01N 21/03 422/400 |
| 2008/0175719 A1* | 7/2008 | Tracey | A61M 1/369 417/38 |
| 2010/0192686 A1* | 8/2010 | Kamen | A61M 1/16 73/290 R |
| 2011/0202031 A1* | 8/2011 | Mihaylov | G01N 1/10 604/408 |
| 2013/0144247 A1* | 6/2013 | Davenport | A61J 1/12 604/404 |
| 2013/0323712 A1* | 12/2013 | Sato | C12M 47/04 435/2 |
| 2014/0299221 A1* | 10/2014 | Lopez | A61M 5/14228 141/1 |
| 2015/0044093 A1* | 2/2015 | Goodwin | A61L 2/007 422/28 |

OTHER PUBLICATIONS

"Multi-Neck Flasks—Sigma-Aldrich Glassware Catalog." Sigma-Aldrich. Nov. 16, 2013. Web. May 11, 2016. <http://www.sigmaaldrich.com/labware/glassware-catalog/flasks-multi-neck.html>.*

* cited by examiner

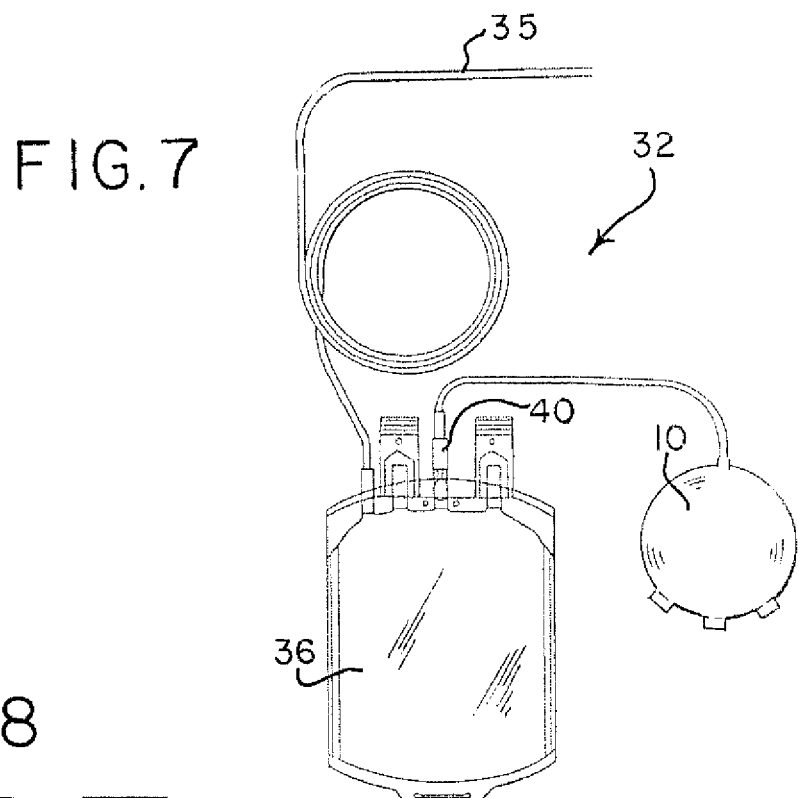
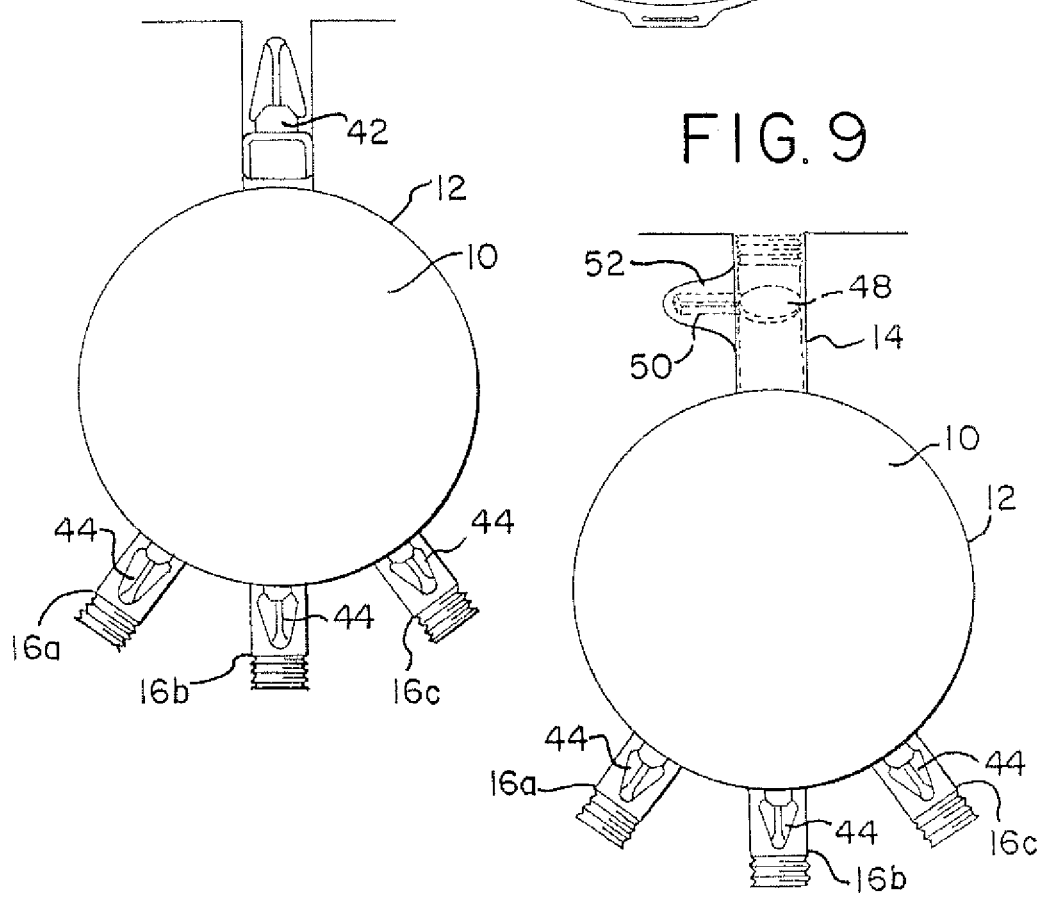

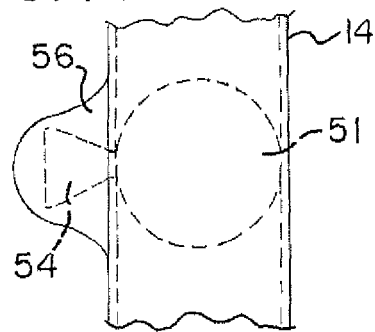
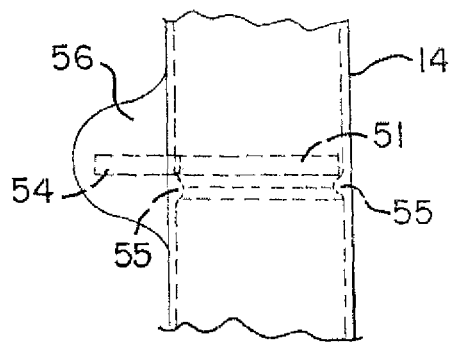
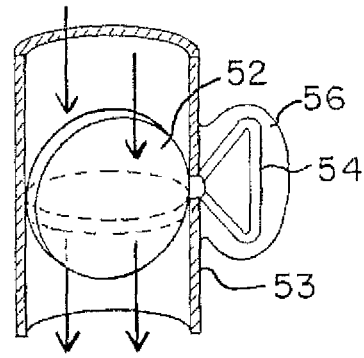
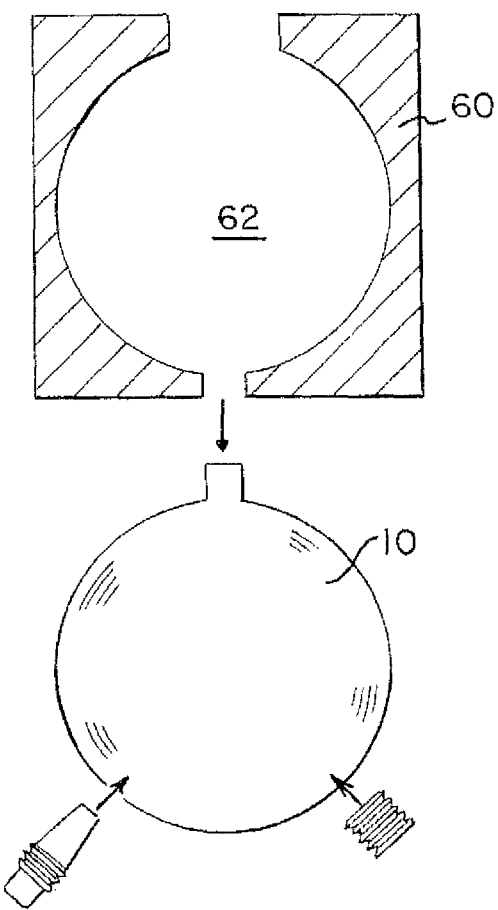
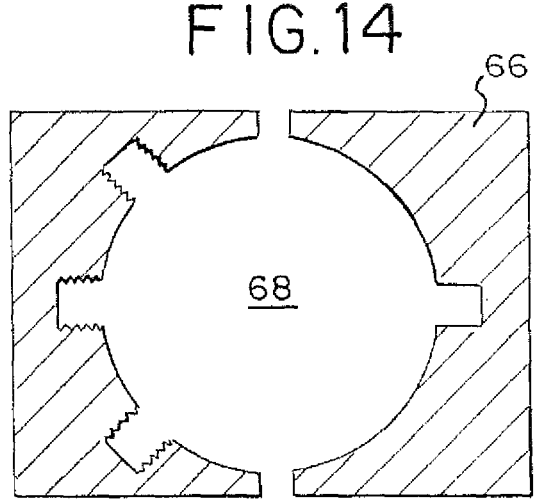

SPHERICAL BIOMEDICAL SAMPLING AND MIXING CONTAINER

FIELD OF THE DISCLOSURE

The present disclosure is directed to biomedical containers for collecting samples of a biological fluid and/or for mixing a biological fluid to provide a substantially homogeneous biological fluid. More particularly, the present disclosure is directed to an at least substantially spherical biomedical container that includes one or more access sites for accessing the contents of the biomedical container. Containers of the type described herein may be used for mixing or sampling a biological fluid and/or for injecting a substance into a larger vessel, or an associated processing kit.

BACKGROUND

In the processing of a biological fluid, such as blood or a blood component, the ability to draw a sample at a selected stage in the processing often provides useful information. For example, obtaining a sample may provide an indication of the composition, concentration or other property of the fluid being processed. Sampling may also provide information about the biological fluid at a selected stage of the processing which may, in turn, dictate future steps in the processing. For at least these reasons, it would be desirable to obtain a sample that is truly representative of the fluid being processed.

Sampling containers are commonly used in biological fluid processing, such as in the collection, manipulation and/or separation of biological fluid. In one non-limiting example, the biological fluid may be a blood product such as whole blood or a component thereof. Where a disposable fluid processing kit is used, a sample "pouch" may be incorporated in the fluid circuit of the kit. Such sampling pouches are often made from two flat sheets of a biocompatible polymeric material wherein the sheets are sealed together along their respective peripheries. The pouch defines an expandable interior chamber which holds the desired fluid and from which samples can be withdrawn. A potential drawback of such flat sheet containers is that they may include corners and/or spaces where fluid may be trapped or otherwise retained. In addition, such containers may have excess surface area where fluid may be trapped, requiring additional manipulation of the container and/or multiple reconnections to obtain additional measurements. Fluid or cellular material trapped in the corners may affect the homogeneity of the fluid to be sampled. This may potentially lead to errors in the measured concentration or composition of the biological fluid, thereby skewing the sample results.

In U.S. Pat. No. 7,699,828, the entire contents of which is hereby incorporated by reference, the interior chamber of the sample pouch has a generally circular profile. The circular profile eliminates corners and the dead spaces where fluid or cellular material may be retained. Fluid containers of the type described in the above-referenced U.S. Pat. No. 7,699,828 are likewise made of flat sheets that are sealed together along their respective peripheries. While such containers are an improvement over sample pouches with less circular interior chamber profiles, they may still allow for cellular material or fluid to become trapped between the sheets of the pouch.

In addition to ability to obtain a representative and homogenous sample, the processing of a biological fluid may, at times, also require the delivery or addition of therapeutic or other agents to the biological fluid. Often, the delivery of the agent is done by injection of the agent into a container interior through a port adapted to receive the injecting syringe. The agent is often required to be mixed with the biological fluid to provide a homogeneous composition. Flat pouches of the type described above, while allowing for mixing, also pose the potential problem of cells being trapped in spaces between the sheets of the container, resulting in less than ideal mixing of the agent and the biological fluid. Additionally, use of such pouches may (where multiple sampling is desired) require several sequential attachments of such containers which may, under certain circumstances, jeopardize the sterility of the processing system. Thus, it would be desirable to provide a biomedical container that eliminates these potential dead zones that may trap cellular material, particularly during the accessing of the container contents to either (a) draw a sample, and/or (b) deliver an agent. In either aspect of biological fluid processing, a higher degree of confidence in the homogeneity of the biological fluid within the biomedical container is desired. It would also be desirable to provide a biomedical container that allows for sampling at various stages of a fluid processing procedure without the need for multiple container connections and disconnections.

SUMMARY

There are several aspects of the present subject matter which may be embodied separately or together in the containers and systems described and claimed below. These aspects may be employed alone or in combination with other aspects of the subject matter described herein, and the description of the aspects together is not intended to preclude the use of these aspects separately or the claiming of such aspects separately or in different combinations as set forth in the claims appended hereto.

In one aspect, the present disclosure is directed to a biomedical container with at least a substantially spherical profile. The container includes a wall defining an at least substantially spherical interior chamber and further includes an inlet and one or more access sites.

In another aspect, the present disclosure is directed to a disposable biological fluid processing kit including a venipuncture access device, a biological fluid collection container, and a flow path between said venipuncture access device and a biomedical container with at least a substantially spherical outer wall defining at least a substantially spherical interior chamber. The container includes an inlet and one or more access sites.

BRIEF DESCRIPTION OF THE DRAWINGS

FIG. 7 is a plan view of another embodiment of a disposable fluid processing kit with a biomedical container in accordance with the present disclosure;

FIG. 8 is a plan view of another embodiment of a biomedical container in accordance with the present disclosure;

FIG. 9 is a plan view of still another embodiment of a biomedical container in accordance with the present disclosure;

FIG. 10 is a an enlarged, partial view of the inlet of the biomedical container of the present disclosure with an alternative embodiment of the flow control device in an "open-flow" position within the inlet of the container;

FIG. 11 is an enlarged, partial view of the inlet of FIG. 10 in a "closed-flow" position;

FIG. 12 is an enlarged, partial, perspective view of the openable inlet to the biomedical container of FIGS. 10 and 11 with the inlet in an open condition when the flow control device is in both the open-flow position, which is shown in solid lines, and in a closed condition when the flow control device is in the closed-flow position, which is shown in broken lines;

FIG. 13 is a schematic view of the method of making the biomedical container of the present disclosure; and FIG. 14 is a schematic view of an alternative molding apparatus which may be used in making one embodiment of the biomedical container of the present disclosure.

DETAILED DESCRIPTION OF THE EMBODIMENTS

Figure 1:
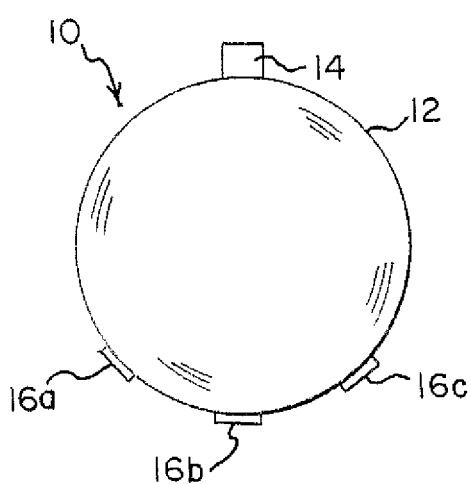
FIG. 1 is a plan view of a biomedical container in accordance with the present disclosure.
Figure 2:
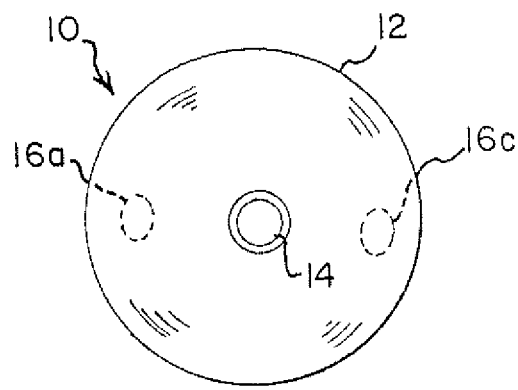
FIG. 2 is a top view of the biomedical container of FIG. 1.

Turning now to the Figures, shown in FIGS. 1 and 2 is a biomedical container 10 in accordance with the present disclosure. As shown in FIGS. 1 and 2, biomedical container has at least a substantially spherical shape. As used herein, the term "at least a substantially spherical shape" or "at least substantially spherical" includes, without limitation, substantially spherical and perfectly or close to perfectly spherical. Biomedical container 10 includes an at least substantially spherical wall 12 that defines an at least a substantially spherical chamber 13 (FIG. 4) for receiving a biological or other fluid. The volume of interior chamber 13 may be any volume desired or required for the processing of the biological fluid. Typically, and without limitation, the volume of interior chamber 13 may be between 5-50 ml or, more typically, 5-30 ml.

In one embodiment, biomedical container 10 may include inlet 14. Inlet 14 defines a flow path to interior chamber 13. As will be described in greater detail below, inlet 14 may be provided with an openable and/or closeable fluid blocking member.

Biomedical container 10 may further include at least one access site 16. Shown in FIG. 1 are three access sites, 16a, 16b, and 16c. It will be understood that the number of access sites 16 is not critical and may include any number of access sites required or desired without affecting the desired firmness and resiliency of the outer container wall 12. Access site 16 allows access, in a sterile manner, from outside of container 10 to the interior chamber 13 and the contents therein.

Figure 3:
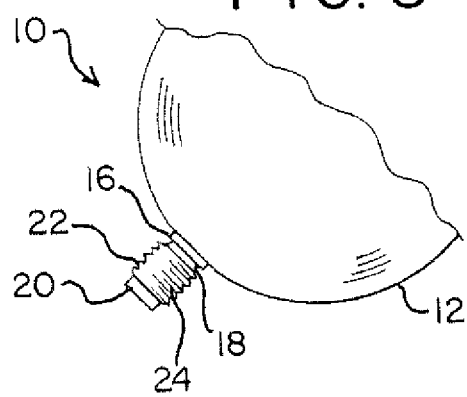
FIG. 3 is a partial view of the biomedical container of FIGS. 1 and 2 with an embodiment of a pierceable access site.

In one embodiment, access site 16 may include a resealable injection site. An access site 16 with a resealable injection site allows access to the interior chamber by piercing a septum by a needle or other external piercing device. Such access site 16 may be used to withdraw samples from interior chamber 13 of biomedical container 10, or deliver an agent to the biological fluid within container 10. The septum reseals itself after the withdrawal of the needle or other piercing device. As shown in FIG. 3, access site 16 may include a luer member 18 that includes a pierceable membrane 20. Luer member 18 may further include a connection surface 22 that allows connection between container 10 and a separate sample vial or other collection device that engages access site 16. In one example, access site may be an Interlink® injection site available from Baxter Healthcare Corporation of Deerfield, Ill.

Figure 4:
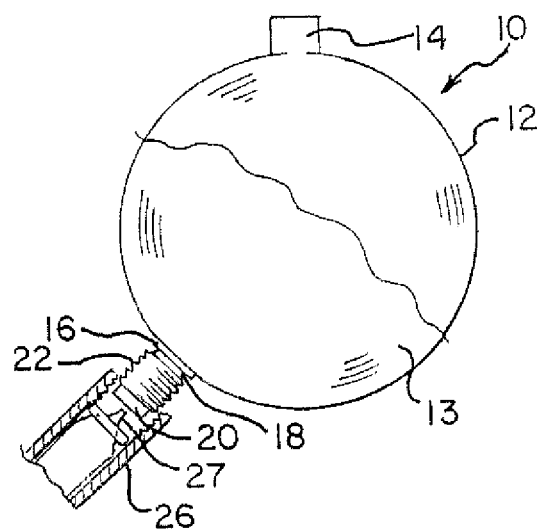
FIG. 4 is a plan view of the biomedical container of FIG. 3 with the access site being engaged by piercing collection device.

As shown in FIG. 3, connection surface 22 may include a thread 24 adapted to receive a corresponding threaded surface of a sample/injection device 26 shown in FIG. 4. Sample device 26 with corresponding threads that attach to access site 16 may include a piercing member 27 that can be advanced through and penetrates resealable septum 20. An example of such a sampling/injection device 26 is described in U.S. Patent Application "Sterile Connection Syringe Assemblies," filed simultaneously herewith and identified by the contents of which are incorporated herein by reference.

Figure 5:
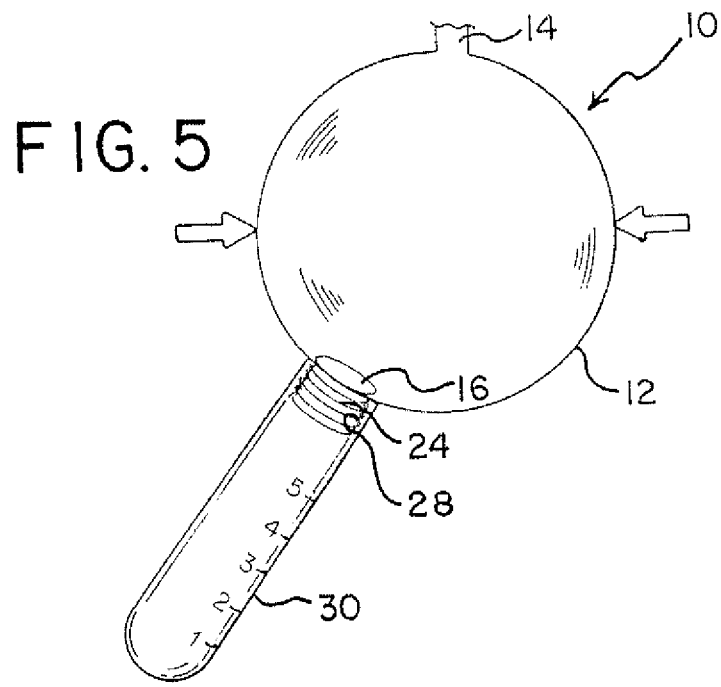
FIG. 5 is a plan view of a biomedical container with a non-pierceable access site being engaged by a different embodiment of a collection device.

Of course, it will be appreciated that there may be other ways of joining a sample collection vial, tube, or other container to access site 16 of biomedical container 10. As shown, for example, in FIG. 5, access site 16 may include a threaded surface 24 that allows for attachment of a sample vial/tube 30, which has a corresponding threaded surface 28. Instead of a pierceable septum, access site 16 of FIG. 5 may be provided as a portion of container wall 12 that is made of different material than the material of container wall 12. In one embodiment, the different material selected for access site 16 of FIG. 5 may be such that upon application of pressure (as indicated by arrows), the material gives way and allows fluid to be collected in vial/tube 30.

Figure 6:
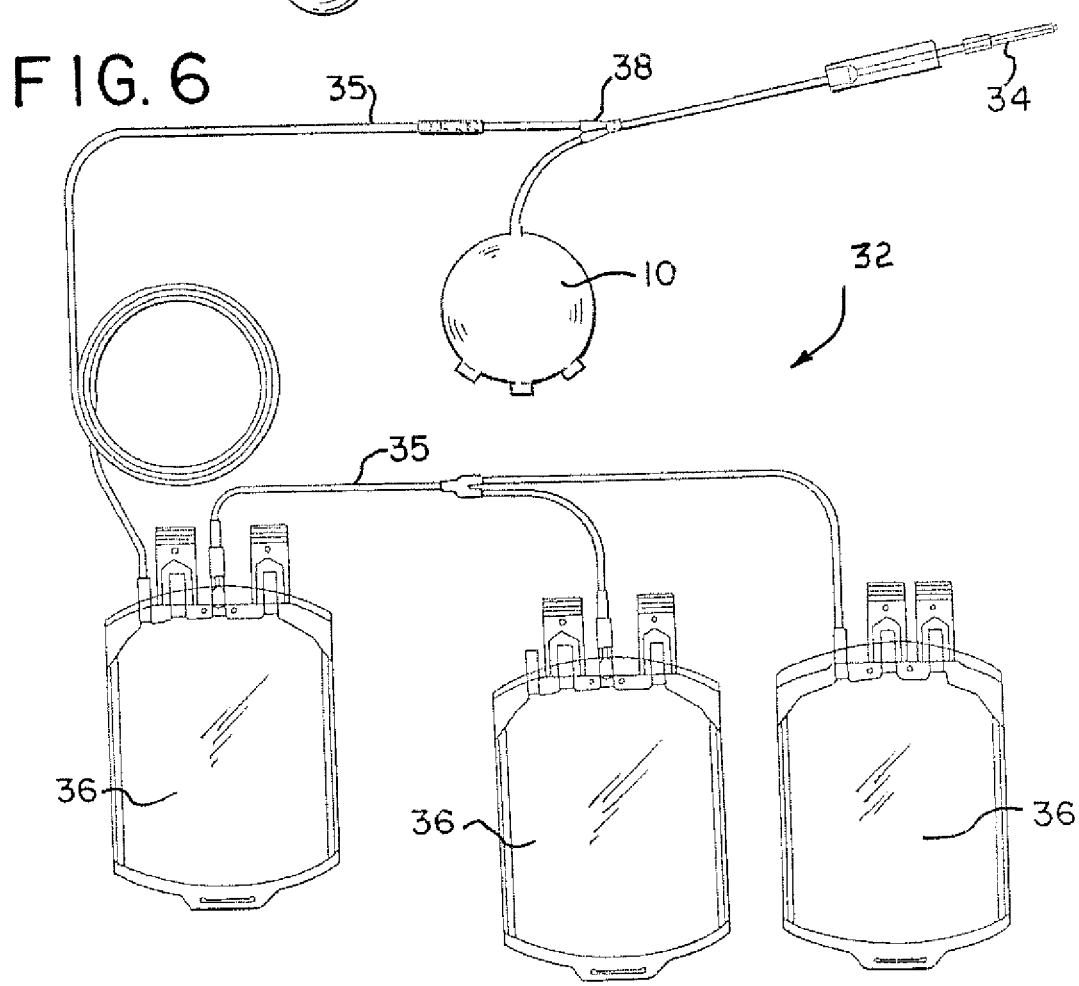
FIG. 6 is a plan view of a disposable fluid processing kit with a biomedical container in accordance with the present disclosure.

Biomedical containers of the type described herein may be incorporated into fluid processing sets for the collection or other processing of biological fluid. As shown in FIG. 6, biomedical container 10 may be part of a larger disposable biological fluid processing kit 32 and incorporated into the fluid circuit thereof. As shown in FIG. 6, kit 32 may include a venipuncture needle 34 or other similar device for accessing and withdrawing biological fluid from a patient, donor, or other source. The disposable processing kit 32 may further include tubing 35 that defines flow paths leading to one or more containers 36. Biomedical container 10 may be located anywhere in the fluid circuit of kit 32. As shown in FIG. 6, for example, biomedical container 10 may be connected in fluid communication with branching member 38, which allows an initial draw of fluid to be diverted to biomedical container 10 prior to collection in any one of containers 36.

In an alternative embodiment, biomedical container 10 may be directly connected to one of the containers 36, as shown in FIG. 7. In that embodiment, biomedical container 10 may be connected through port 40 of container 36. This allows the blood biological fluid collected in container 36 to be sampled. It will be appreciated that container 36 may have a different configuration with, for example, port 40 located elsewhere.

Other elements that may be included in biomedical container 10 are shown in FIGS. 8-12. As shown, for example, in FIG. 8, inlet port 14 and/or access site 16a-c may include openable fluid blocking members or flow control device, which may be opened by the user at a selected time. In one embodiment, flow device 42 and 44 may be or include frangible (i.e., breakable) members commonly used in blood processing kits and described in more detail in U.S. Pat. No. 4,294,247, the contents of which are hereby incorporated by reference.

In one embodiment, frangible member 42 may be located in the flow path of inlet 14 of biomedical container 10. For example, when biomedical container 10 is part of a larger fluid processing kit 32, as shown in FIG. 6, and a sample is to be collected, flow into biomedical container 10 may be established by breaking frangible member 42 at the selected time. Similarly, when access to the contents of biomedical container 10 is desired, access site 16 (*a-c*), which may also be provided with frangible members 44, may be opened to allow such access. In similar fashion, members 44 may be broken to establish flow between the interior chamber 13 of biomedical container 10, and sample vials, tubes, or other containers attached to access sites 16*a-c*.

Other ways for blocking and otherwise controlling fluid flow through biomedical container 10 are shown in FIGS. 9-13. In FIG. 9, there is shown a valve 48 that blocks a fluid from entering chamber 13 of container 10. Valve 48 may be a non-permeable disk made of rigid plastic and a biocompatible material. Valve 48 may have an outer diameter that is at least equal to the inner diameter of the flow path in inlet 14. Valve 48 may be connected to a rigid pull tab 50 across the wall of inlet 14, as shown. Pulling on tab 50 away from the outer wall of inlet 14 establishes a fluid gap in the flow path of inlet 14, thereby allowing fluid to flow into interior chamber 13. As further shown in FIG. 9, pull tab 50 may be enveloped and sealed with a flexible sleeve 52 that seals the connection site between pull tab 50 and blocking member or valve 48. Sleeve 52 prevents liquid from escaping through the connection site between pull tab 50 and valve 48 and also preserves the sterility of biomedical container 10 and the fluid contained therein.

An alternative openable valve is shown in FIGS. 10-12. As in the embodiment of FIG. 9, valve 51 may be a disk that blocks the flow path of inlet 14. Valve 51 preferably has an outer diameter that is at least equal to the inner diameter of the flow path in inlet 14. Valve 51 may be connected to tab 54 through wall 53 of inlet 14 (FIG. 12). In the embodiment of FIGS. 10-12, instead of pulling tab 54, tab 54 may be twisted up to, for example, 90° to open the flow path within inlet 14 and allow fluid flow into interior chamber 13. The inner surface of wall 53 may include a retaining member, such as annular rib 55 that extends from the inner surface of wall 53, to allow the disk valve to remain in a horizontal position during a closed-flow condition, as shown in FIG. 11. As in the embodiment of FIG. 9, tab 54 may likewise be sealed with a protective sleeve 56 that prevents leakage of fluid and preserves the sterility of biomedical container 10 and the contents therein.

Container 10 of the present disclosure may be made of any suitable biocompatible material. In one embodiment, the material should be sufficiently flexible such that adequate mixing of the contents can be achieved by manual pressure and/or such that adequate pressure may be applied to express fluid from interior chamber 13 to an attached sample, tube, vial and the like, and/or potentially back into a remainder of kit 32. In addition, the material of biomedical container 10 should be sufficiently resilient and possess a suitable shape memory to recover its original at least substantially spherical shape after squeezing or after pressure has been applied to outer wall 12 of biomedical container 10. The material used for biomedical container 10 should also be suitable for bonding, such as solvent bonding of additional components to container 10. For example, where luer connectors 18 of the type described above are provided as access sites, such connectors may be solvent bonded to container wall 12. The material for biomedical containers should also be suitable for sterilization by sterilizing methods commonly used for medical products, including but not limited to autoclaving (i.e., steam sterilization). Furthermore, the materials for biomedical container 10 should be capable of being blow molded or otherwise formed into an at least substantially spherical shape. Examples of suitable materials include but are not limited to polytetrafluoroethylene (PTFE), plasticized polyvinylchloride (PVC), and polyethylene. Other suitable polymeric or other materials may include polycarbonate for frangible members 42/44.

As shown in FIGS. 13-14, biomedical container 10 may be molded into the at least substantially spherical container with inlet 14, whereby luer connectors, or threaded members, or burstable wall portions may be attached post-molding. Shown in FIG. 13 is a mold 60, which defines a spherical mold cavity 62, resulting in such spherical container 10. Alternatively, as shown in FIG. 14, container 10 may be blow molded wherein the mold cavity 68 of mold 66 defines spouts for inlet 14 and access sites 16.

In accordance with the present disclosure, biomedical container 10 described herein provides a container that substantially prevents the formation of dead zones where cellular material or other biological fluid may become trapped thereby affecting the homogeneity of the fluid and potentially skewing the sampling results. To achieve this, biomedical container 10 of the present disclosure may be characterized by a high volume and low surface area. Accordingly, the dimensions of biomedical container 10 may be such that the ratio of surface area to volume results in a low number. For example, where the ratio of surface area to volume is expressed by the following formula, $$\frac{SA}{V} = \frac{4\pi r^2 \cdot 3}{4\pi r^3}$$

it may be desirable that the radius is greater than 3 (e.g., cm, mm, inches, etc.) to arrive at a ratio of less than 1.0.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is as set forth in the following claims, and it is understood that the claims may be directed to the features hereof, including as combinations of features that are individually disclosed or claimed herein.

Other Aspects

In a first aspect, a biomedical container is provided. The container has an at least substantially spherical profile and includes a wall defining an at least substantially spherical interior chamber. The container includes an inlet and one or more access sites.

A second aspect of the present subject matter includes the container in accordance with the first aspect wherein the one or more access site(s) includes an engagement member for receiving an external vessel.

A third aspect of the present subject matter includes the container in accordance with the second aspect wherein the engagement member includes a threaded region for engagement with a complimentary threaded region of the vessel.

A fourth aspect of the present subject matter includes the biomedical container in accordance with any one of the first through third aspects wherein the one or more access site(s) includes a pierceable membrane.

A fifth aspect of the present subject matter includes the biomedical container in accordance with any one of the first through fourth aspects wherein the one or more access site(s) is in openable flow communication with the interior chamber.

A sixth aspect of the present subject matter includes the biomedical container in accordance with any one of the first through fifth aspects wherein the wall is made of a polymeric material.

A seventh aspect of the present subject matter includes the biomedical container in accordance with any one of the first through sixth aspects wherein the container is formed of a blow-moldable material.

An eighth aspect of the present subject matter includes the biomedical container in accordance with any one of the sixth through seventh aspects wherein the polymeric and/or blow-moldable material is selected from the group consisting of polytetrafluoroethylene, polyvinyl chloride and polyethylene.

A ninth aspect of the present subject matter includes the biomedical container in accordance with any one of the sixth through eighth aspects wherein the polymeric and/or blow-moldable material is sufficiently flexible such that the container can be compressed to a non-spherical profile and has a shape memory that allows the container to return from the non-spherical profile to its at least substantially spherical profile.

A tenth aspect of the present subject matter includes the biomedical container in accordance with any one of the first through ninth aspects wherein the container wall has an inner surface of a selected surface area and the interior chamber has a selected volume.

An eleventh aspect of the present subject matter includes the biomedical container in accordance with any one of the first through tenth aspects wherein the container has a surface area (SA) to volume (V) ratio of less than 1.

A twelfth aspect of the present subject matter includes the biomedical container in accordance with the seventh aspect wherein the at least one said access site includes a material different from the blow-moldable material.

A thirteenth aspect of the present subject matter includes the biomedical container in accordance with any one of the first through twelfth aspects including a plurality of access sites.

A fourteenth aspect of the present subject matter includes the biomedical container in accordance with any one of the first through thirteenth aspects wherein the at least one of the access sites includes a pierceable membrane.

A fifteenth aspect of the present subject matter includes the biomedical container in accordance with any one of first through thirteenth aspects wherein the at least one of the access sites includes a frangible member.

A sixteenth aspect of the present subject matter includes the biomedical container in accordance with any one of the first through thirteenth aspects wherein the at least one of the access sites includes a valve.

In a seventeenth aspect a disposable biological fluid processing kit is provided. The kit includes a venipuncture access device, a biological fluid collection container, a flow path between said venipuncture access device and said biological fluid collection container, and a biomedical container with a substantially spherical outer wall defining at least a substantially spherical interior chamber. The biomedical container includes an inlet and one or more access sites.

An eighteenth aspect of the present subject matter includes the disposable biological fluid processing kit in accordance with the seventeenth aspect wherein the biomedical container is in openable flow communication with the venipuncture access device.

A nineteenth aspect of the present subject matter includes the disposable biological fluid processing kit in accordance with the eighteenth aspect wherein the biomedical container is provided between the venipuncture access device and the biological fluid container.

A twentieth aspect of the present subject matter includes the disposable biological fluid processing kit in accordance with the seventeenth aspect wherein the biological fluid collection container includes a port and a second flow path communicating with the port and the biomedical container.

A twenty first aspect of the present subject matter includes the disposable processing kit of any one of the seventeenth through twentieth aspects wherein the kit is sterilizable by steam sterilization.

The invention claimed is:

1. A biomedical container comprising a spherical profile, integrally molded flexible wall devoid of sealed-together multiple sheets comprising a polymeric material and defining a spherical interior, said polymeric material of said integral container wall being sufficiently flexible such that said container can be compressed to a non-spherical profile and has a shape memory that allows said container to return from said non-spherical profile to said spherical profile, said container wall comprising an integrally-formed inlet and a plurality of sealed and openable access sites, wherein said inlet comprises a flow path and includes a valve within said flow path, said valve being openable and closeable by an actuator located outside said flow path.

2. The biomedical container of claim 1 wherein each of said access sites comprises a connection surface for receiving an external vessel in mating engagement therewith.

3. The biomedical container of claim 2 wherein said connection surface comprises a threaded region for engagement with a complimentary threaded region of said vessel.

4. The biomedical container of claim 1 wherein at east one of said plurality of access comprises a pierceable membrane.

5. The biomedical container of claim 1 wherein said access sites are in operable flow communication with said interior chamber.

6. The biomedical container of claim 1 wherein said, integrally molded flexible wall is formed of a blow-moldable material.

7. The biomedical container of claim 1 wherein said polymeric material is selected from the group consisting of polytetrafluoroethylene, polyvinyl chloride and polyethylene.

8. The biomedical container claim 1 wherein said wall has an inner surface of a selected surface area and said interior chamber comprises a selected volume such that a surface area to volume ratio of the container is less than 1.

9. The biomedical container of claim 6 wherein at least one of said plurality of access sites comprises a material different from said blow-moldable material.

10. The biomedical container of claim 1 wherein at least one of said plurality of access sites comprises a frangible member.

11. The biomedical container of claim 1 wherein at least one of said plurality of access sites comprises a valve.

12. A disposable biological fluid processing kit comprising
   a venipuncture access device,
   a biological fluid collection container,
   a flow path between said venipuncture access device and said biological fluid collection container and
   a biomedical container comprising a spherical profile, integrally molded flexible outer wall devoid of sealed-together multiple sheets comprising a polymeric material and defining a spherical interior chamber devoid of dead zones for cellular material or fluid to become trapped, said integral outer wall being sufficiently flexible such that said spherical biomedical container can be compressed to a non-spherical profile and has a shape memory that allows said container to return from said non-spherical profile to said spherical profile, said integral wall comprising an integrally-formed inlet port and a plurality of sealed and openable access sites and wherein said container has a selected volume and a selected radius such that the surface area to volume ratio is less than 1.

13. The disposable biological fluid processing kit of claim 12 wherein said biomedical container is in openable flow communication with said venipuncture access device.

14. The disposable biological fluid processing kit of claim 13 wherein said biomedical container is provided between said venipuncture access device and said biological fluid collection container.

15. The disposable biological fluid processing kit of claim 12 wherein said biological fluid collection container comprises a port and a second flow path communicating with said inlet port and said biomedical container.

16. The disposable processing kit of claim 12 wherein said kit is sterilizable by steam sterilization.

17. The disposable processing kit of claim 15 wherein said inlet port of said biomedical container includes a valve for controlling flow into said interior chamber.

18. The disposable processing kit of claim 17 wherein said biomedical container comprises a tab for actuating said valve.

19. The disposable processing kit of claim 18 wherein said tab comprises a pull tab.

20. The disposable processing kit of claim 18 wherein said tab is enveloped with a flexible and grippable sleeve.

21. The disposable processing kit of claim 17 wherein said valve comprises a disk rotatable by up to at least about 90°.

22. The biomedical container of claim 1 further comprising a valve in said inlet for controlling flow into said interior chamber.

23. The biomedical container of claim 22 wherein said valve comprises a grippable tab for actuating said valve.

* * * * *